United States Patent [19]

Singerman

[11] 4,032,649
[45] June 28, 1977

[54] 2,3-DIHYDRO-2,2-DIMETHYL-7-BENZO[b]THIENYL N-METHYLCARBAMATE AND USE AS AN INSECTICIDE

[75] Inventor: Gary M. Singerman, Allegheny County, Pa.

[73] Assignee: Gulf Oil Corporation, Pittsburgh, Pa.

[22] Filed: Nov. 12, 1975

[21] Appl. No.: 631,009

[52] U.S. Cl. .......................... 424/275; 260/330.5; 260/455 A; 260/578; 260/622 R
[51] Int. Cl.² ...................................... C07D 333/64
[58] Field of Search ................ 260/330.5, 346.2 R; 424/275

[56] References Cited

UNITED STATES PATENTS

| 3,288,808 | 11/1966 | Kilsheimer et al. | 260/330.5 |
|---|---|---|---|
| 3,470,299 | 9/1969 | Heiss | 424/285 |
| 3,474,171 | 10/1969 | Scharpf | 424/285 |
| 3,547,955 | 12/1970 | Scharpf | 260/346.2 |
| 3,564,605 | 2/1971 | Scharpf | 424/285 |
| 3,819,683 | 6/1974 | Krebs et al. | 260/479 C |

*Primary Examiner*—Cecilia M. S. Jaisle
*Attorney, Agent, or Firm*—Carl A. Cline

[57] ABSTRACT

Insects are combated selectively in the presence of other forms of animal life by applying to the locus of the insects an effective amount of 2,3-dihydro-2,2-dimethyl-7-benzo[b]thienyl N-methylcarbamate, a compound with less mammalian toxicity than closely related carbamate insecticides.

3 Claims, No Drawings

2,3-DIHYDRO-2,2-DIMETHYL-7-BENZO[b]THIENYL N-METHYLCARBAMATE AND USE AS AN INSECTICIDE

DESCRIPTION OF THE INVENTION

Background and Summary

In the control of insects with insecticides, continuous use of a few effective substances at rather high application rates has resulted in repeated nearly complete kills over a period of about three decades. As a consequence of this practice, present day insects are descended from survivors of almost total kills. As might be expected, many species of insects are now resistant to most of the common insecticides. Some of the most common and useful insecticides employed during the last quarter of a century have also been used to excess and residues of these insecticides have accumulated in the tissues of the animal inhabitants of the earth. As a result of these events it has been necessary to discover and put to use new insecticides. The general trend has been toward use of compounds of greater overall toxicity which do not cause the accumulation of residues. The new compounds, however, are often very toxic to birds and mammals and must be used with great care.

One of the useful newer insecticides is carbofuran, which is disclosed in U.S. Pat. No. 3,474,171. This compound kills a rather large variety of both insects and acarids. Unfortunately the compound is also quite toxic to other animals. In tests of oral toxicity on mice this commercial insecticide has displayed an $LD_{50}$ as low as 4. I have discovered, however, that the compound 2,3-dihydro-2,2-dimethyl-7-benzo[b]thienyl N-methylcarbamate, which differs from the commercial insecticide by only one sulfur atom, under the same test conditions exhibits an $LD_{50}$ greater than 100. The new compound is more selective also in its action toward insects and is considerably less toxic than the prior art compound on acarids. As a consequence of the compound's unique properties, it may be used more selectively on specific insect problems with less injury of competing and predatory insects and less danger to wildlife.

DETAILED DESCRIPTION

Synthesis of the Insecticide

A convenient laboratory synthesis route is outlined in equations 1 to 8 and is illustrated in the specific procedures disclosed below.

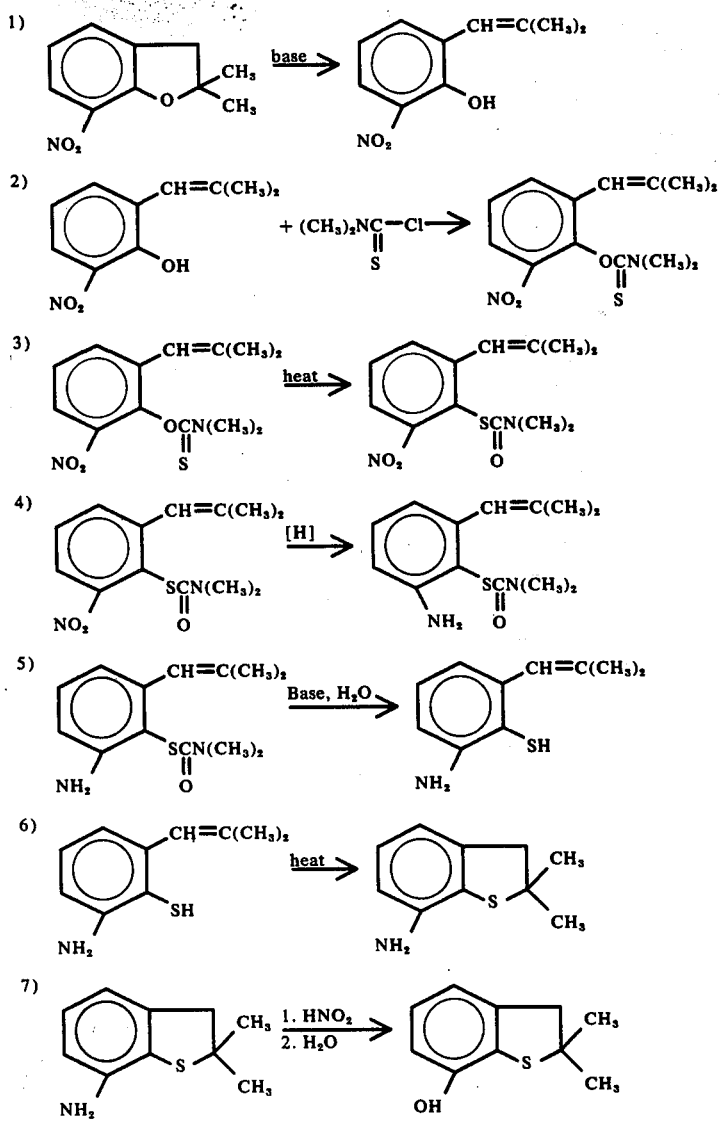

8) 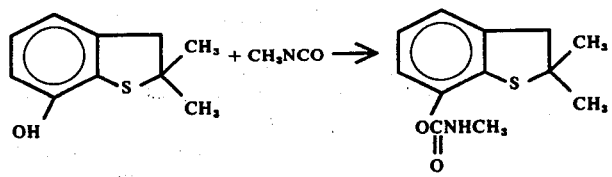

The starting material for this synthesis, 2,3-dihydro-2,2-dimethyl-7-nitrobenzofuran (Eq. 1), may be obtained from 2-nitrophenol and methallyl chloride according to the teaching of U.S. Pat. No. 3,320,286. Alternatively, the starting material may be prepared by nitration of 2,2-dimethylcoumaran, a known compound [J.C. Martini, et al, J. Org. Chem., 35, 2904 (1970)].

In Equation 1, it is seen that the cyclic ether, 2,3-dihydro-2,2-dimethyl-7-nitrobenzofuran is cleaved in basic medium to 2-isobutenyl-6-nitrophenol. The mild conditions under which this cleavage occurs are quite surprising in view of the well-known fact that ethers are comparatively unreactive compounds. According to R. T. Morrison and R. N. Boyd [Organic Chemistry, Allyn and Bacon, Inc., 1959, pp. 417, 418], "The ether linkage is quite stable toward bases, oxidizing agents, and reducing agents. In so far as the ether linkage itself is concerned, ethers undergo just one kind of reaction, cleavage by acids. - - - Cleavage takes place only under quite vigorous conditions: concentrated acids (usually HI or HBr) and high temperature." In general, this statement is correct, except a few isolated cases have been reported wherein an ether linkage is cleaved under strongly basic and vigorous conditions. One such example is cleavage of the ether linkage in 2,3-dihydrobenzofuran by metallic sodium in boiling pyridine solution [J. Gripenberg and T. Hase, Acta Chem. Scand. 20 (6), 1561 (1966)]. I have found surprisingly, that 2,3-dihydro-2,2-dimethyl-7-nitrobenzofuran is smoothly cleaved to 2-isobutenyl-6-nitrophenol (Eq. 1) in less than one hour at room temperature by potassium t-butoxide in dimethylsulfoxide solution. It is possible that even milder bases could effect this cleavage. The remaining reactions (Eq. 2–8) employed in the preparation of the insecticide cannot be considered surprising or novel, although as far as is known the products from each of these reactions are new compounds.

PREPARATION OF 2,3-DIHYDRO-2,2-DIMETHYL-7-NITROBENZOFURAN

Procedure A. This compound was obtained from 2-nitrophenol and methallyl chloride as described in U.S. Pat. No. 3,320,286.

Procedure B. 2,2-dimethylcoumaran was obtained from phenol and isobutyraldehyde as described by J. C. Martini, et al, J. Org. Chem., 35, 2904 (1970). A mixture of 48.9 g (0.33 mole) 2,2-dimethylcoumaran and 60 g acetic anhydride was placed in a 500 ml 3-neck, round-bottom reaction flask fitted with stirrer, addition funnel and thermometer. The mixture was cooled in an ice bath below 10° C. To the stirred solution was added dropwise over one hour a cold solution of 20 g glacial acetic acid, 20 g acetic anhydride and 31.5 g concentrated nitric acid (specific gravity 1.42, 70% HNO₃), keeping the temperature of the reaction mass at 5°–10° throughout the addition. After completion of addition, the reaction mass was stirred at 5°–10° for an additional 15 minutes and was then allowed to stand at room temperature 1.5 hours. The reaction mixture was poured into 400 ml of ice and water and extracted with ether. The ether extract was washed first with water then with aqueous 7% potassium hydroxide solution until the aqueous phase remained basic, and finally with water. It was then dried over magnesium sulfate. Magnesium sulfate was removed by filtration and ether was removed from the filtrate by evaporation on a rotatory evaporator. Vacuum distillation of a portion of the residue gave 4.1 g recovered 2,2-dimethylcoumaran, b.p. 52°–55° at 2.5 mm. Hg., and 32.7 g of an oily mixture of 2,3-dihydro-2,2-dimethyl-7-nitrobenzofuran and 2,3-dihydro-2,2-dimethyl-5-nitrobenzofuran, b.p. 117°–128° at 2.0 mm. Hg., identified by proton magnetic resonance (pmr). The mixture appeared to contain approximately equal amounts of the two isomers by pmr. The two isomers may be separated by fractional recrystallization. For example, recrystallization of a portion of the mixture from a 1:2 mixture of water:dimethylsulfoxide provides yellow crystals of the 5-nitro isomer (identified by pmr), leaving the more soluble 7-nitro isomer in solution. However, it is unnecessary to separate the two isomers, since pure 2-isobutenyl-6-nitrophenol can be obtained directly from the mixture (see preparation of 2-isobutenyl-6-nitrophenol, Procedure B).

SYNTHESIS OF 2-ISOBUTENYL-6-NITROPHENOL (EQ. 1)

Procedure A. A solution of 16.1 g (0.0834 mole) 2,3-dihydro-2,2-dimethyl-7-nitrobenzofuran (obtained from 2-nitrophenol and methallyl chloride according to U.S. Pat. No. 3,320,286) and 100 ml dry dimethylsulfoxide was chilled in an ice bath and stirred magnetically. To it was added a slurry of 11.2 g (0.1 mole) potassium t-butoxide and 20 ml dimethylsufoxide. After a few minutes the mixture was removed from the ice bath and stirred at room temperature for 45 minutes. The mixture was poured into 500 ml water and washed with ether (discard ether). The aqueous phase was acidified with 50% aqueous hydrochloric acid and extracted with ether. The ether phase was washed with water and dried over magnesium sulfate. The magnesium sulfate was removed by filtration and ether was removed from the filtrate by evaporation on a rotatory evaporator. The residue was distilled to give 8.7 g of oily 2-isobutenyl-6-nitrophenol, bp 90°–93° at 0.1 mm Hg. This compound was identified by its proton magnetic resonance (pmr) spectrum which in CDCl₃ solution showed two singlet absorptions at 1.73 and 1.88 ppm (δ) for the methyl group protons of the isobutenyl substituent, a singlet absorption at 6.13 δ for the olefinic proton of the isobutenyl substituent, and complex absorption between 6.60 and 7.80 δ for the aromatic protons.

Procedure B. A mixture of 2,3-dihydro-2,2-dimethyl-7-nitrobenzofuran and 2,3-dihydro-2,2-dimethyl-5-nitrobenzofuran (24.3 g), prepared by nitration of 2,2-dimethylcoumaran as described above, was dissolved in 100 ml dimethylsulfoxide, and treated with 16.0 g potassium t-butoxide as described in Procedure A. After processing the reaction mixture according to Procedure A, the product was steam distilled to give pure 2-isobutenyl-6-nitrophenol from the aqueous distillate by extraction with ether.

SYNTHESIS OF 0-(2-ISOBUTENYL-6-NITROPHENYL)-N,N-DIMETHYLTHIOCARBAMATE (EQ. 2).

Procedure A. Following the procedure of M. S. Newman and H. A. Karnes [J. Org. Chem. 31, 3980 (1966)], a solution of 1.7 g (0.00881 mole) 2-isobutenyl-6-nitrophenol, 30 ml water, and 0.56 g (0.01 mole) potassium hydroxide was stirred 10 minutes at room temperature, and to it was added a solution of 2.5 g (0.02 mole) dimethylthiocarbamoyl chloride and 15 ml tetrahydrofuran. The mixture was stirred at room temperature 5.5 hours, then 100 ml water was added to it. The mixture was made basic with aqueous potassium hydroxide and extracted with ether. The ethereal extract was washed with aqueous sodium chloride solution and dried over magnesium sulfate. The magnesium sulfate was removed by filtration and ether was removed from the filtrate by evaporation on a rotatory evaporator to give 2.1 g crystalline 0-(2-isobutenyl-6-nitrophenyl)-N,N-dimethylthiocarbamate. This compound was identified by its pmr spectrum which showed in $CCl_4$ solution two singlet absorptions at 1.73 and 1.88 $\delta$ for the methyl group protons of the isobutenyl substituent, two singlets separated by 2 cps and centered at 3.32 $\delta$ for the methyl group protons of the dimethylthiocarbamoyl group, a broad singlet at 5.98 $\delta$ for the olefinic proton of the isobutenyl substituent, and a multiplet absorption between 6.97 and 7.83 $\delta$ for the aromatic protons.

Procedure B. A solution of 26.2 g (0.13575 mole) 2-isobutenyl-6-nitrophenol and 250 ml dry tetrahydrofuran was stirred magnetically and chilled in an ice bath while to it was added a slurry of 0.14 moles sodium hydride and 20 ml tetrahydrofuran. The mixture was stirred 20 minutes at room temperature, and to it was added a solution of 17.3 g (0.14 mole) dimethylthiocarbamoyl chloride and 50 ml tetrahydrofuran. The mixture was stirred at room temperature for 45 minutes, then stirred and refluxed for 2.5 hours. After stirring overnight at room temperature, tetrahydrofuran was removed from the mixture by evaporation on a rotatory evaporator, and 200 ml water was added to the residue. The aqueous mixture was extracted with chloroform. The chloroform extract was washed with aqueous sodium chloride and dried over magnesium sulfate. The magnesium sulfate was removed by filtration and chloroform was stripped from the filtrate on a rotatory evaporator to give 37.5 g of crystalline 0-(2-isobutenyl-6-nitrophenyl)-N,N-dimethylthiocarbamate.

SYNTHESIS OF S-(2-ISOBUTENYL-6-NITROPHENYL)-N,N-DIMETHYLTHIOCARBAMATE (EQ. 3)

Following the procedure of M. S. Newman and H. A. Karnes [J. Org. Chem. 31, 3980 (1966)], 2.0 g of 0-(2-isobutenyl-6-nitrophenyl)-N,N-dimethylthiocarbamate was heated under dry nitrogen at 180°–185° for 45 minutes to give dark, oily S-(2-isobutenyl-6-nitrophenyl)-N,N-dimethylthiocarbamate. This structure was identified by its pmr spectrum which showed in $CCl_4$ solution two singlet absorptions at 1.68 and 1.88 $\delta$ for the methyl group protons of the isobutenyl substituent, a singlet absorption at 2.93 $\delta$ for the methyl group protons of the dimethylcarbamoyl substituent, a broad singlet at 6.13 $\delta$ for the olefinic proton, and a multiplet absorption between 7.52 and 7.10 $\delta$ for the aromatic protons. The infrared spectrum of this material shows strong absorption at 5.9 microns due to the carbonyl group of the dimethylcarbamoyl substituent.

SYNTHESIS OF S-(2-ISOBUTENYL-6-AMINOPHENYL)-N,N-DIMETHYLTHIOCARBAMATE (EQ. 4)

A solution of 4.0 ml glacial acetic acid and 160 ml water was heated to 60° C and the heat source was removed. The solution was stirred mechanically and 28.0 g iron powder was added, then 12.0 g crude S-(2-isobutenyl-6-nitrophenyl)-N,N-dimethylthiocarbamate was added. After an initial exotherm, the heat source was replaced and the reaction mixture was stirred and heated to 85° C. The heat source was again removed and the mixture was stirred and allowed to cool to 60° C and was then suction filtered through Celite. Both the filter cake and filtrate was extracted with chloroform. The combined chloroform extracts were dried over magnesium sulfate. Magnesium sulfate was removed by filtration and chloroform was stripped from the filtrate on a rotatory evaporator to give 9.2 crystalline S-(2-isobutenyl-6-aminophenyl)-N,N-dimethylthiocarbamate, melting range 89°–99° C. This structure was identified by its pmr spectrum, which showed in $CDCl_3$ solution two singlet absorptions at 1.67 and 1.83 $\delta$ for the methyl group protons of the isobutenyl substituent, a singlet at 2.97 $\delta$ for the methyl group protons of the dimethylcarbamoyl substituent, a broad absorption centered at 4.10 $\delta$ for the amino group protons, a broad singlet absorption at 6.15 $\delta$ for the olefinic proton of the isobutenyl substituent, and a multiplet absorption between 6.37 and 7.10 $\delta$ for the aromatic protons.

SYNTHESIS OF 2-AMINO-6-ISOBUTENYLTHIOPHENOL (EQ. 5)

A mixture of 27.5 g crude S-(2-isobutenyl-6-aminophenyl)-N,N-dimethylthiocarbamate, 27.0 g potassium hydroxide, 100 ml water, and 200 ml methanol was stirred and refluxed overnight. Methanol was removed from the mixture by evaporation on a rotatory evaporator and replaced with water. The aqueous mixture was washed with ether (discard ether). The aqueous phase was neutralized with 50% aqueous hydrochloric acid and extracted with ether. The ethereal extract was washed with water and dried over magnesium sulfate. Magnesium sulfate was removed by filtration and ether was stripped from the filtrate on a rotatory evaporator to give 17.7 g crude 2-amino-6-isobutenylthiophenol as a dark oil. This material was used without further purification in the next step (EQ. 6). Its pmr spectrum in $CDCl_3$ solution showed that hydrolysis was complete; absorption due to the methyl group protons of the dimethylcarbamoyl group of the starting material was absent.

SYNTHESIS OF 7-AMINO-2,3-DIHYDRO-2,2-DIMETHYLBENZO[B]THIOPHENE (EQ. 6)

17.7 g crude 2-amino-6-isobutenylthiophenol was heated under nitrogen at 180°–190° C for 40 minutes, and then was distilled to give 6.4 g of the title compound as a yellow oil, bp 115°–120° C at 0.4 mm. Hg. This structure was identified by its pmr spectrum which showed in $CDCl_3$ solution a singlet absorption at 1.53 δ for the protons of the two methyl groups in the 2-position of the ring system, a singlet absorption at 3.01 δ for the protons in the 3-position, a singlet absorption at 3.50 δ for the protons of the 7-amino group, and a multiplet absorption between 6.23 and 6.87 δ for the aromatic protons.

SYNTHESIS OF 7-HYDROXY-2,3-DIHYDRO-2,2-DIMETHYLBENZO[B]THIOPHENE (EQ. 7)

A solution of 6.5 g (0.03631 mole) 7-amino-2,3-dihydro-2,2-dimethylbenzo[b]thiophene, 300 ml water, and 20 ml concentrated sulfuric acid was cooled to 0° C, and to it was added a solution of 2.5 g (0.03631 mole) sodium nitrite and 20 ml water, keeping the temperature of the reaction mixture at 0°–10° C during addition of the sodium nitrite and for 5 minutes thereafter to complete formation of 2,3-dihydro-2,2-dimethyl-7-benzo[b]thienyldiazonium sulfate. The diazonium salt solution was then added dropwise, rapidly, through through an addition funnel to a vigorously boiling solution of 1 liter water saturated with cupric sulfate. The diazonium salt solution was kept in an ice bath and added portionwise to the addition funnel so that its temperature did not exceed 20° C. Since the title compound steam distills as it forms, the steam from the boiling cupric sulfate solution was condensed in a downward-pointing condenser and collected throughout the addition of the diazonium salt solution and for 10 minutes thereafter, when nitrogen evolution appeared complete. The cupric sulfate solution was cooled, and both it and the aqueous distillate were extracted with ether. The ether extracts were combined and extracted with aqueous potassium hydroxide solution (discard ether). The strongly basic aqueous solution was acidified with 50% aqueous hydrochloric acid and extracted with ether. The ether extract was washed with aqueous sodium chloride and dried over magnesium sulfate. Magnesium sulfate was removed by filtration and ether was stripped from the filtrate to give a black, oily residue. The residue was distilled to give 3.1 g of the title compound, b.p. 109°–115° C at 0.16 mm. Hg. The product crystallized as a yellow solid in the condenser during distillation, m.p. 87°–92°, and also partially sublimed during the distillation. This structure was identified by its pmr spectrum which showed in $CDCl_3$ solution a singlet absorption at 1.52 δ for the protons of the two methyl groups in the 2-position of the ring system, a singlet absorption at 3.02 δ for the protons in the 3-position, a singlet at 4.87 δ for the 7-hydroxy proton, and a multiplet absorption between 6.37 and 6.90 δ for the aromatic protons.

PREPARATION OF 2,3-DIHYDRO-2,2-DIMETHYL-7-BENZO[B]THIENYL METHYLCARBAMATE (EQ. 8)

A solution of 2.9 g (0.0161 mole) 7-hydroxy-2,3-dihydro-2,2-dimethylbenzo[b]thiophene, 1.2 g (0.02 mole) methylisocyanate 20 ml ether and 4 drops of triethylamine was allowed to stand, stoppered, overnight at room temperature to precipitate 3.3 g of the title compound as white crystals, m.p. 163°–166°, isolated by suction filtration. An additional 0.5 g of less pure product was isolated by evaporation of ether from the filtrate. This structure was identified by its pmr spectrum which showed in $CDCl_3$ solution a singlet absorption at 1.52 δ for the protons of the two methyl groups in the 2-position of the ring system, a doublet absorption centered at 2.77 δ for the methyl group protons of the methylcarbamoyl group, a singlet absorption at 3.05 δ for the protons in the 3-position, a broad absorption centered at 4.93 δ for the amido proton of the methylcarbamoyl group, and a singlet absorption at 6.83 δ for the aromatic protons. The aromatic protons appear as a singlet because they are magnetically equivalent. The pmr spectrum of this compound is almost identical to that of its oxygen-containing analog, 2,3-dihydro-2,2-dimethyl-7-benzofuranyl methylcarbamate (carbofuran) with one major exception: the aromatic protons of carbofuran are not magnetically equivalent and appear in $CDCl_3$ solution as a complex multiplet absorption between 6.43 and 6.93 δ.

Elemental Analysis:

|          | Theory | Found |
|----------|--------|-------|
| Carbon   | 60.73  | 60.60 |
| Hydrogen | 6.37   | 6.16  |
| Sulfur   | 13.51  | 13.64 |
| Nitrogen | 5.90   | 5.77  |
| Oxygen   | 13.48  | 13.54 |

COMBATING INSECTS

In combating insects only a sufficient percentage of the insect population should be killed so that economic damage to the crop is avoided. Total kills are neither necessary nor desirable. However, in laboratory evaluation, much of the data will be used for the purpose of comparing insecticides with each other and for deciding on rates of application for specific circumstances. Total kills are therefore more often obtained in the laboratory than in commercial practice. This is true of the tests described below.

The following procedures were employed:

Three 5 oz paper cups containing Henderson dwarf lima bean plants and one 5 oz paper cup containing Orange Gem nasturtiums, all growing in vermiculite, are placed on a turntable and sprayed to thorough wetness with 25 ml of a solution of the candidate chemical at the appropriate concentration. Nasturtiums are already infested with 50–100 bean aphids (BA). A bean plant in one paper cup is already infested with 50–100 two-spotted mites (TSM). Leaves from the two remaining bean plants are removed following spraying and placed in disposable petri dishes with 5 southern armyworm (SA) larvae in one petri dish, and 5 Mexican bean beetle (MBB) larvae in the other petri dish. The rating is done approximately 48 hours after spraying as follows:

| BA | TSM |
|---|---|
| 0 = none dead | 0 = no dead adults |
| 1 = 1–25% dead | 1 = 1–25% dead adults |
| 2 = 26–50% dead | 2 = 26–50% dead adults |

-continued

| | |
|---|---|
| 3 = 51–75%dead | 3 = 51–75% dead adults |
| 4 = 76–99% + dead | 4 = 76–99% dead adults |
| 5 = 100% MBB | 5 = 100% dead adults SA |
| 0 = less than 1% larvae dead | 0 = less than 1% larvae dead |
| 1 = 1–25% larvae dead | 1 = 1–25% larvae dead |
| 2 = 26–50% larvae dead | 2 = 26–50% larvae dead |
| 3 = 51–75% larvae dead | 3 = 51–75% larvae dead |
| 4 = 76–99% larvae dead | 4 = 76–99% larvae dead |
| 5 = 100% larvae dead | 5 = 100% larvae dead |

Results are recorded in Table 1.

TABLE 1

INSECTICIDAL ACTIVITY OF NEW COMPOUND

| Insecticide Concentration (ppm) in spray mixture | MBB | SA | BA | TSM |
|---|---|---|---|---|
| 500 | 5 | 5 | 5 | 4 |
| 250 | 5 | 1 | 5 | 2 |
| 125 | 5 | 0 | 5 | 1 |
| 62 | 5 | 0 | 5 | 0 |
| 31 | 5 | 0 | 5 | 0 |
| 15 | 5 | 0 | 4 | 0 |
| 7.8 | 5 | 0 | 3 | 0 |

When a solution of the new insecticide (62 ppm) was applied to the plant roots instead of the foliage, systemic activity was found. This is shown in Table II, in which the same scoring system was used as in Table 1, and carbofuran was included as a standard.

TABLE II

| New Insecticide | | | | Carbofuran | | | |
|---|---|---|---|---|---|---|---|
| MBB | SA | BA | TSM | MBB | SA | BA | TSM |
| 5 | 1 | 5 | 0 | 5 | 5 | 5 | 0 |

The more selective nature of the new insecticide is evident from these data.

In use of the insecticide it is not necessary to apply the substance to insects directly. Application to the locus, or area in which the insects live, is sufficient. As demonstrated above, the compound displays systemic activity, so that absorption by plants on which insects are feeding, or will feed in the future is included within the concept of application to the locus of the insects. It will be noticed that effective concentrations of insecticide in an aqueous spray mixture may be quite low. Because of the high degree of insecticidal activity it is preferred practice to apply the insecticide in combination with an inert diluent, preferably water, and with the use of a surface active agent to aid in uniform distribution and wetting of plants. Other diluents, such as dry powders and oils may be used, according to conventional formulating practices.

I claim:
1. The insecticidal compound 2,3-dihydro-2,2-dimethyl-7-benzo[b]thienyl N-methylcarbamate having the structural formula

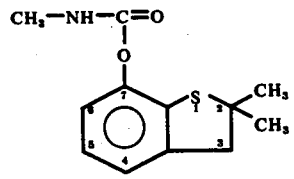

2. The insecticidal composition comprising an inert diluent, a surface active agent and an effective amount of 2,3-dihydro-2,2-dimethyl-7-benzo[b]thienyl N-methylcarbamate.
3. The method of combating insects which comprises applying to the locus of the insects an effective amount of 2,3-dihydro-2,2-dimethyl-7-benzo[b]thienyl N-methylcarbamate in combination with an inert diluent and a surface active agent.

* * * * *